(12) United States Patent
Weingaertner et al.

(10) Patent No.: US 9,366,795 B2
(45) Date of Patent: Jun. 14, 2016

(54) ILLUMINATION DEVICE WITH AN EXTENDED USEABLE SPECTRUM

(71) Applicant: Schott AG, Mainz (DE)

(72) Inventors: Thomas Weingaertner, Gau-Algesheim (DE); Lothar Willmes, Hallgarten (DE); Bernd Schultheis, Schwabenheim (DE)

(73) Assignee: SCHOTT AG, Mainz (DE)

( * ) Notice: Subject to any disclaimer, the term of this patent is extended or adjusted under 35 U.S.C. 154(b) by 184 days.

(21) Appl. No.: 14/274,822

(22) Filed: May 12, 2014

(65) Prior Publication Data

US 2015/0016140 A1 Jan. 15, 2015

(30) Foreign Application Priority Data

May 14, 2013 (DE) .......................... 10 2013 208 838

(51) Int. Cl.
*F21V 8/00* (2006.01)
*G02B 6/02* (2006.01)
(Continued)

(52) U.S. Cl.
CPC ............ *G02B 6/0008* (2013.01); *A61B 1/0684* (2013.01); *A61B 1/07* (2013.01); *A61B 1/227* (2013.01); *A61C 1/088* (2013.01); *A61C 19/004* (2013.01); *C03C 3/062* (2013.01); *C03C 3/064* (2013.01); *C03C 3/066* (2013.01); *C03C 3/076* (2013.01); *C03C 3/078* (2013.01); *C03C 3/085* (2013.01); *C03C 3/087* (2013.01); *C03C 3/089* (2013.01); *C03C 3/091* (2013.01); *C03C 3/093* (2013.01); *C03C 3/095* (2013.01); *C03C 3/097* (2013.01); *C03C 3/11* (2013.01); *C03C 3/112* (2013.01); *G02B 6/02395* (2013.01); *G02B 6/04* (2013.01)

(58) Field of Classification Search
CPC ........ A61B 1/0684; A61B 1/07; A61B 1/227; A61C 1/088; A61C 19/004; C03C 3/11; C03C 3/062; C03C 3/064; C03C 3/066; C03C 3/076; C03C 3/078; C03C 3/085; C03C 3/087; C03C 3/089; C03C 3/091; C03C 3/093; C03C 3/095; C03C 3/097; C03C 3/112; G02B 6/04; G02B 6/0008; G02B 6/02395
See application file for complete search history.

(56) References Cited

U.S. PATENT DOCUMENTS 7,833,073 B2 * 11/2010 Ogawa ................ C04B 35/111
445/24
2012/0302423 A1 * 11/2012 Kinoshita ............. C03C 3/068
501/37

FOREIGN PATENT DOCUMENTS

| DE | 1030945 A1 | 9/2004 |
|---|---|---|
| DE | 102004034603 B4 | 2/2006 |
| DE | 102009004159 A1 | 7/2010 |

OTHER PUBLICATIONS

Wang, et al. "Diagnosis of oral cancer by light-induced autofluorescence spectroscopy using double excitation wavelengths", Oral Oncology 35, 1999, pp. 144-150.

*Primary Examiner* — Stephen F Husar
(74) *Attorney, Agent, or Firm* — Ohlandt, Greeley, Ruggiero & Perle, LLP

(57) ABSTRACT

An illumination device for irradiating objects with electromagnetic radiation is provided. The illumination device includes at least one light guide and a radiation source that emits electromagnetic radiation in the spectral region from 320 nm to 420 nm into the light guide. The light guide is formed of a glass that has a spectral transmittance of at least 70% at 350 nm and is selected from the system of lead-free silicate-tin glasses.

13 Claims, 5 Drawing Sheets

Figure 1:
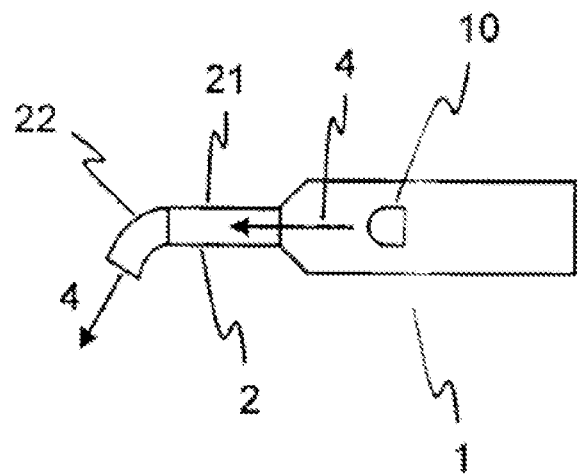

(51) Int. Cl.

| | | | |
|---|---|---|---|
| *G02B 6/04* | (2006.01) | *C03C 3/087* | (2006.01) |
| *A61B 1/06* | (2006.01) | *C03C 3/089* | (2006.01) |
| *A61B 1/07* | (2006.01) | *C03C 3/091* | (2006.01) |
| *A61B 1/227* | (2006.01) | *C03C 3/093* | (2006.01) |
| *C03C 3/062* | (2006.01) | *C03C 3/095* | (2006.01) |
| *C03C 3/064* | (2006.01) | *C03C 3/097* | (2006.01) |
| *C03C 3/066* | (2006.01) | *C03C 3/11* | (2006.01) |
| *C03C 3/076* | (2006.01) | *C03C 3/112* | (2006.01) |
| *C03C 3/078* | (2006.01) | *A61C 13/15* | (2006.01) |
| *C03C 3/085* | (2006.01) | *A61C 1/08* | (2006.01) |

ILLUMINATION DEVICE WITH AN EXTENDED USEABLE SPECTRUM

The invention relates to an illumination device with expanded useful spectrum. The illumination device can be utilized for diverse fields of application, but particularly in dental medicine and/or in general medicine, surgery, diagnostics, and/or, however, also in automatic image processing (English: Machine Vision).

Illumination devices for these fields of application are known from the prior art. For dental applications, for example, glass fiber rods that are pulled in a drawing process and/or tapered into conical shapes, and/or bent in an associated downstream bending process are utilized in such devices. Usually, manufactured glass fiber rods are bonded in metal or stainless-steel sheathing or encapsulated with a plastic by means of an injection molding process. All materials should be particularly chemically resistant, in particular against water vapor, since these components in many cases must be steam-sterilized, as a rule at temperatures of more than 120° C., typically more than 130° C.

Typical requirements are, for example, stability for more than 500 autoclaving cycles at 134° C. at 3 bars and 5-10 min. holding time (sterilizing time). The cycle time in this case amounts to 60 min. In particular, illumination devices are used in this field of application as so-called dental hardening or curing devices, with which tooth fillings based on synthetic resin are hardened by means of blue light. Depending on the type of resin base used in each case, different wavelength regions of the electromagnetic radiation emitted from the illumination device are viewed as particularly suitable, in particular, the wavelength region from 380 nm to 510 nm having focal points with respect to an optimal absorption of the resin material at 380 nm to 390 nm, 460 nm to 470 nm and/or 490 nm to 500 nm.

Another known application example of the above-named illumination devices relates to pressed glass fiber rods, which are utilized for illumination in turbine casings of dental drills. For this purpose, glass fiber rods are shaped two-dimensionally or three-dimensionally in a pressing process and, subsequently, the end surfaces are ground and polished. By means of this rigid light guide, electromagnetic radiation in the visible spectral region is guided from a light source disposed in a handle to the head of the turbine casing in order to illuminate in this way the tooth to be treated when drilling. Also, a high transmission is necessary here, particularly in the entire visible region of light, i.e., from approximately 400 to 700 nm, in order to be able to assure a high illumination of light. In addition, a high color fidelity is also expected here, which is reflected in the so-called CRI value (color rendering index). If this value is high, e.g., >80, there is only a slight discoloring when observing the tooth surface or tissue surface. Low CRI values lead to discoloration, so that in the most unfavorable case, differences in color of the tooth or of the surrounding tissue are falsely rendered or they cannot be identified. Thus, here also, the transmission in the glass fiber rods, a transmission that is as high and as uniform as possible, viewed over the visible spectrum, is necessary.

A manufacturing method as well as devices for producing pressed glass fiber rods is known from DE 10 2004 034 603 B4. The production of metered goods associated therewith is described in DE 10 2009 004 159 A1.

Other applications of the above-named illumination devices target the identification of cancer cells, e.g., in the mouth cavity. Generally, tissue regions are irradiated with UV light for this purpose, and the long-wave, back-scattered and/or emitted radiation is spectrally analyzed. Thus, for example, based on the ratios of specific back-scattered and/or emitted wavelength regions, a cancerous alteration in the cells can be inferred. The wavelength regions of the back-scattered and/or emitted radiation lie, e.g., in the regions of 325 to 335 nm, 375 to 385 nm, as well as 465 to 475 nm (see "Diagnosis of oral cancer by light-induced autofluorescence spectroscopy using double excitation wavelengths", Oral Oncology 35 (1999), pp. 144-150).

Common to the illumination devices of the prior art is the fact that the light guides used limit the fields of application. Previously used light guides made of glass in fact generally have a better transmission than those made of plastic; however, even the best previously known glass materials that are processed as light guides have an increasing absorption, the shorter the wavelength of the radiation that is guided in the light guide. The transmission usually decreases in the blue spectral region, so that at the very least, the color rendering quality is reduced when irradiating an object with an above-named illumination device.

This can particularly increase the hardening time in dental hardening or curing applications, but can also limit the diagnosis of a dentist, and, in particular, the usefulness of the devices in other diagnostic applications, particularly in the described methods for identifying cancer cells.

Against this background, the object of the invention is to provide an illumination device that has an expanded useful spectrum when compared with the illumination devices of the prior art, particularly a light guide with an improved transmission especially in the spectral range of 320 nm to 420 nm.

The object is achieved by the illumination device according to the independent claims. Preferred embodiments and applications thereof result from the dependent claims.

An illumination device according to the invention comprises at least one light guide and one radiation source. In the operating state, the radiation source emits electromagnetic radiation comprising at least one sector from the spectral region from 320 nm to 420 nm into the light guide, which is guided from the light guide to the object to be irradiated. The at least one light guide comprises a glass that is irradiated by the electromagnetic radiation in the operating state and that has a spectral transmittance of at least 70% at the wavelength of 350 nm. The glass of the light guide contains no lead and is a glass from the system of silicate-tin glasses. Advantageously, the spectral transmittance amounts to at least 60% at 340. Likewise advantageously, the spectral transmittance in the wavelength region from 400 nm to 700 nm has a plateau that is characterized by the fact that the spectral transmittance at one wavelength in this wavelength region differs by 6% at most from the spectral transmittance of another wavelength within this region.

Silicate-tin glasses are generally understood to be glasses that contain at least $SiO_2$ and $SnO_2$ in oxide form in their list of components.

In the operating state, the radiation source emits electromagnetic radiation at least in a sector of the spectral region from 320 nm to 420 nm. This means that least one emission wavelength must lie in this region. Other wavelength regions are additionally possible and advantageous. Particularly advantageously, an irradiation device according to the invention can also emit electromagnetic radiation in the visible spectral region, so that a spectral region from approximately 380 nm to 780 nm is included. It is likewise possible that the radiation source also emits in regions of the infrared spectral region and this radiation is advantageously guided by the light guide.

The term spectral transmittance is known to the person skilled in the art. It describes the transmission of the glass at the named wavelength. The spectral transmittance at 360 nm is determined by measuring instruments known to the person skilled in the art, in particular by spectrophotometers.

Except for perhaps impurities, the glass of the light guide contains no lead. Impurities are components that result due to impure raw materials and/or contamination during glass manufacture and cannot be removed with justifiable expenditure. Usually, the maximum concentration of impurities is 3 ppm. The absence of lead makes it possible to dispense with this substance that is damaging to the environment during production, but particularly also during application. Lead can also be dissolved out of the glass during autoclaving procedures for sterilizing the light guide, which can reduce the long-term stability of the light guide and, in fact, its transmission.

Preferably, the lead-free glass from the system of silicate-tin glasses comprises the components (in wt. % based on oxide):

|  | from | to |
|---|---|---|
| $B_2O_3$ | 0 | 24 |
| $SiO_2$ | 23 | 62.1 |
| $Al_2O_3$ | 0 | 10 |
| $Li_2O$ | 0 | 10 |
| $Na_2O$ | 0 | 18.5 |
| $K_2O$ | 0 | 25.7 |
| BaO | 0 | 57.8 |
| ZnO | 0 | 40 |
| $La_2O_3$ | 0 | 25 |
| $ZrO_2$ | 0 | 10 |
| $HfO_2$ | 0 | 14.2 |
| $SnO_2$ | >0 | 2 |
| MgO | 0 | 8 |
| CaO | 0 | 8 |
| SrO | 0 | 24.4 |
| $Ta_2O_5$ | 0 | 22 |
| $Y_2O_3$ | 0 | 11.9 |
| $Rb_2O$ | 0 | 15 |
| $Cs_2O$ | 0 | 21 |
| $GeO_2$ | 0 | 7.5 |
| F | 0 | 2 |
| Σ $R_2O$ | 5 | 20 |
| Σ MgO, CaO, SrO, ZnO | 20 | 42 |

$R_2O$ here stands for the named monovalent components. The alkaline-earths MgO, CaO and/or SrO and/or additionally ZnO are contained from at least 20% up to 42% in the glass of this group.

All data with respect to the composition of glasses is given in wt. % based on oxide in this description, as long as it is not explicitly stated otherwise.

Advantageously, in this system of silicate-tin glasses, the weight ratio of $SiO_2$ to $B_2O_3$ is more than 5. Likewise of advantage is a total content of the components MgO, CaO, BaO, SrO, $La_2O_3$, $Ta_2O_5$, $ZrO_2$ and $HfO_2$ of at least 40%. Likewise of advantage is a proportion of $Sn^{2+}$ of 5% at most in the total tin content, particularly of advantage is a content of $SnO_2$ of at least 0.01 and at most 1%. The refractive index $n_d$ of the glasses of this group particularly advantageously lies between 1.53 and 1.74. The contents of $SnO_2$ can be achieved by addition during synthesis and/or by inserting a tin refining during the melting of the glasses.

Particularly advantageously, the lead-free glasses in the system of silicate-tin glasses comprise (in wt. % based on oxide):

|  | from | to |
|---|---|---|
| $B_2O_3$ | 0 | 0 |
| $SiO_2$ | 35 | 50 |
| $Al_2O_3$ | 1 | 10 |
| $Li_2O$ | 0 | 1 |
| $Na_2O$ | 0 | 15 |
| $K_2O$ | 0 | 15 |
| BaO | 20 | 30 |
| ZnO | 0 | 15 |
| $La_2O_3$ | 0 | 10 |
| $ZrO_2$ | 0.1 | 10 |
| $P_2O_5$ | 0 | 6 |
| $HfO_2$ | 0 | 0 |
| $SnO_2$ | >0 | 0.4 |
| MgO | 0 | 8 |
| CaO | 0 | 8 |
| SrO | 0 | 8 |
| $Y_2O_3$ | 0 | 0 |
| $Rb_2O$ | 0 | 0 |
| $Cs_2O$ | 0 | 1 |
| $GeO_2$ | 0 | 0 |
| Σ $R_2O$ | 5 | 15 |
| Σ MgO, CaO, SrO | 0 | 8 |

Especially of advantage, the lead-free glasses in the system of silicate-tin glasses comprise (in wt. % based on oxide):

|  | from | to |
|---|---|---|
| $B_2O_3$ | 0 | 1 |
| $SiO_2$ | 42 | 53 |
| $Al_2O_3$ | 0 | 1.5 |
| $Li_2O$ | 0 | 3 |
| $Na_2O$ | 0 | 14 |
| $K_2O$ | 0 | 12 |
| BaO | 0 | 0.9 |
| ZnO | 16 | 38 |
| $La_2O_3$ | 0 | 0 |
| $ZrO_2$ | 0 | 2 |
| $HfO_2$ | 0 | 0 |
| $SnO_2$ | >0 | 0.4 |
| MgO | 0 | 6 |
| CaO | 0 | 5 |
| SrO | 0 | 6 |
| $Y_2O_3$ | 0 | 0 |
| $Rb_2O$ | 0 | 0 |
| $Cs_2O$ | 0 | 0 |
| $GeO_2$ | 0 | 0 |
| F | 0 | 2 |
| Σ $R_2O$ | >2 |  |

Likewise, especially of advantage, the lead-free glasses in the system of silicate-tin glasses comprise (in wt. % based on oxide):

|  | From | to |
|---|---|---|
| $B_2O_3$ | 6 | 24 |
| $SiO_2$ | 25 | 55 |
| $Al_2O_3$ | 0 | 0 |
| $Li_2O$ | 0 | 10 |
| $Na_2O$ | 0 | 14 |
| $K_2O$ | 0 | 4.4 |
| BaO | 16 | 42 |
| ZnO | 3 | 40 |
| $La_2O_3$ | 0 | 0 |
| $ZrO_2$ | 0 | 1 |
| $HfO_2$ | 0 | 0 |
| $SnO_2$ | >0 | 0.4 |
| MgO | 0 | 3 |
| CaO | 0 | 3 |
| SrO | 0 | 4 |
| $Y_2O_3$ | 0 | 0 |
| $Rb_2O$ | 0 | 0 |

-continued

|  | From | to |
|---|---|---|
| $Cs_2O$ | 0 | 0 |
| $GeO_2$ | 0 | 0 |
| F | 0 | 3 |

The following silicate-tin glasses with the following composition in wt. % based on oxide are also especially advantageous:

|  | from | to |
|---|---|---|
| $B_2O_3$ | 0 | 5.1 |
| $SiO_2$ | 28.3 | 62.1 |
| $Al_2O_3$ | 0 | 0 |
| $Li_2O$ | 0.08 | 9.9 |
| $Na_2O$ | 0 | 18.5 |
| $K_2O$ | 0 | 25.7 |
| BaO | 0.5 | 12.8 |
| ZnO | 13 | 37.2 |
| $La_2O_3$ | 1.6 | 14.5 |
| $ZrO_2$ | 2.1 | 9.8 |
| $HfO_2$ | 0.04 | 14.2 |
| $SnO_2$ | >0 | 0.3 |
| MgO | 0 | 1.3 |
| CaO | 0 | 1.9 |
| SrO | 0 | 9 |
| $Y_2O_3$ | 0 | 0 |
| $Rb_2O$ | 0 | 15 |
| $Cs_2O$ | 0 | 21 |
| $GeO_2$ | 0 | 7.5 |

Other silicate-tin glasses with the following composition in wt. % based on oxide are also most especially advantageous:

|  | from | to |
|---|---|---|
| $B_2O_3$ | 0 | 15 |
| $SiO_2$ | 34.5 | 51.8 |
| $Al_2O_3$ | 0.1 | 2.8 |
| $Li_2O$ | 0 | 0.2 |
| $Na_2O$ | 2.7 | 8.9 |
| $K_2O$ | 0.1 | 1.4 |
| BaO | 14.7 | 57.8 |
| ZnO | 0 | 17 |
| $La_2O_3$ | 0 | 16.4 |
| $ZrO_2$ | 0 | 6.9 |
| $HfO_2$ | 0 | 0 |
| $SnO_2$ | >0 | 0.4 |
| MgO | 0 | 2.9 |
| CaO | 0 | 4.8 |
| SrO | 0 | 24.4 |
| $Y_2O_3$ | 0 | 11.9 |
| $Rb_2O$ | 0 | 3.9 |
| $Cs_2O$ | 0 | 5.8 |
| $GeO_2$ | 0 | 0 |

In turn, other silicate-tin glasses with the following composition in wt. % based on oxide are also especially advantageous:

|  | from | to |
|---|---|---|
| $B_2O_3$ | 0.1 | <5 |
| $SiO_2$ | 23 | 35 |
| $Al_2O_3$ | 0 | 1 |
| $Li_2O$ | 0.2 | 4 |
| $Na_2O$ | 0 | <3 |
| $K_2O$ | 0 | 3 |
| BaO | 5 | 35 |
| ZnO | 8 | 25 |
| $La_2O_3$ | 10 | 25 |
| $ZrO_2$ | 0.5 | 9 |
| $HfO_2$ | 0.01 | 2 |
| $SnO_2$ | 0.01 | 2 |
| CaO | 0 | 3 |
| SrO | 0 | 1 |
| $Ta_2O_5$ | 0 | 22 |

It is particularly advantageous if the glasses utilized that are made of the named components contain the described percentage limits.

One or a plurality of the following components can be contained: $Cs_2O$, $Rb_2O$, MgO, CaO, SrO, $Gd_2O_3$, $Lu_2O_3$, $Sc_2O_3$, $Y_2O_3$, $In_2O_3$, $Ga_2O_3$ and $WO_3$.

The following components should not be contained in the glass or contained only in concentrations that are caused by the unavoidable impurities of the raw materials: $TiO_2$, $CeO_2$, $Nb_2O_5$, $MoO_3$, $Bi_2O_3$, PbO, CdO, $Tl_2O$, $As_2O_3$, $Sb_2O_3$, $SO_3$, $SeO_2$, $TeO_2$, BeO, radioactive elements and coloring components, as long as not stated otherwise in the text. In particular, $TiO_2$ should be omitted, since this component can lead to a pronounced absorption in the UV region. In advantageous embodiments, the component $WO_3$ is also left out.

The components $TiO_2$, $CeO_2$, $Nb_2O_5$ and/or $Bi_2O_3$ can be contained in the glass of the invention up to a maximum of 0.5 wt. %, advantageously up to 0.3 wt. %, and particularly advantageously up to 0.2 wt. %. In an advantageous embodiment, the glass is free of these components.

Advantageously, the glasses according to the invention are free of optically active components, in particular $Sm_2O_3$, $Nd_2O_3$, $Dy_2O_3$, $Pr_2O_3$, $Eu_2O_3$, $Yb_2O_3$, $Tb_2O_3$, $Er_2O_3$, $Tm_2O_3$ and/or $Ho_2O_3$. $CeO_2$ can serve for stabilization against solarization. Of course, $CeO_2$ absorbs in the UV region, so that advantageous glasses of this invention do not contain $CeO_2$.

The content of the alkaline-earth metal oxide components $La_2O_3$, $Ta_2O_5$, $ZrO_2$ and $HfO_2$ advantageously in total, and particularly for glasses with refractive values of more than 1.65, is at least 40 wt. %, more advantageously at least 42 wt. %, even more advantageously at least 50 wt. %, and most particularly advantageously at least 55 wt. %. If the content of these components is too low, the advantageous refractive index cannot normally be achieved. Based on the formulation, this sum should not exceed a value of 72 wt. %.

The glass can further comprise fluorine or fluoride and/or chlorine or chloride. The content of fluoride advantageously is up to 0.6 wt. %, more advantageously up to 0.55 wt. %. Chloride can be contained in the glass in a content of 0.2 wt. % at most, advantageously up to 0.15 wt. %. Special embodiments of the glass are free of fluorine or fluoride and/or chlorine or chloride.

Advantageously, the glass in the system of the silicate-tin glasses is composed of the named components.

Developments of illumination devices with lead-free glasses made of the system of silicate-alkali-zinc glasses are likewise conceivable. Such a silicate-alkali-zinc glass could particularly contain (in wt. % based on oxide):

|  | from | to |
|---|---|---|
| $SiO_2$ | 39 | 52 |
| $Li_2O$ | 0 | 6 |
| $Na_2O$ | 0 | 8 |
| $K_2O$ | 0 | 8 |

-continued

|  | from | to |
|---|---|---|
| BaO | >0 | 12 |
| ZnO | 18 | 30 |
| $La_2O_3$ | 7 | 12 |
| $ZrO_2$ | >0 | 7 |
| $HfO_2$ | 0 | 4 |
| MgO | 0 | 6 |
| CaO | 0 | 6 |
| SrO | 0 | 12 |
| $As_2O_3$ | 0 | 0.5 |
| F | 0 | 2 |
| $\Sigma\ Li_2O,\ Na_2O,\ K_2O$ | 3 | 19 |

The refractive index $n_d$ of these glasses can particularly lie in the range of 1.50 to 1.60.

Due to the absence of PbO, the described glass types according to the invention are characterized as particularly environmentally friendly. Also, when compared with the prior art, they possess a more uniform transmission in the visible color spectrum and an improved transmission, particularly in the blue spectral region, and also advantageously in the near UV, i.e., the typical wavelength region of the above-named fields of application.

The following table shows several preferred compositions of cladding glasses and/or sheathing glasses that can be used together with the glasses according to the invention. The cladding glasses and/or sheathing glasses preferably contain (in wt. % based on oxide):

| Oxides | Group 1 | Group 2 | Group 3 | Group 4 |
|---|---|---|---|---|
| $SiO_2$ | 70-78 | 63-75 | 75-85 | 62-70 |
| $Al_2O_3$ | 5-10 | 1-7 | 1-5 | 1-10 |
| $B_2O_3$ | 5-14 | 0-3 | 10-14 | >15 |
| $Li_2O$ | 0-2 | 0-1 | 0-3 | 0-2 |
| $Na_2O$ | 0-10 | 8-20 | 2-8 | 0-10 |
| $K_2O$ | 0-10 | 0-6 | 0-1 | 0-10 |
| MgO | 0-1 | 0-5 | none | 0-5 |
| CaO | 0-2 | 1-9 | none | 0-5 |
| SrO | 0-1 | none | none | 0-5 |
| BaO | 0-4 | 0-5 | none | 0-5 |
| F | 0-1 | 0-1 | none | 0-1 |
| Cl | 0-1 | 0-1 | none | 0-1 |
| $Fe_2O_3$ | 0-2 | 0-2 | 0-2 | 0-2 |

In particular, ZnO also can be contained optionally up to 2 wt. %, particularly in the glass of group 4.

A person skilled in the art, based on his expert knowledge, is in a position to also utilize still other cladding glasses and/or sheathing glasses. It cannot be predicted with certainty, however, whether these glasses also harmonize in each case with the core glasses in the presence of the necessary physical properties and whether good step-index fibers result. Therefore, it is recommended to experimentally verify a provided cladding glass-core glass pairing and/or sheathing glass (and, optionally, cladding glass)-core glass pairing for its suitability in the individual specific case.

The named cladding glasses and/or sheathing glasses particularly advantageously are free of lead, cadmium, arsenic, and antimony. Particularly advantageously, they are composed of the named components in the named composition ranges. In particular, glass types that are especially chemically inert and that thus can particularly well withstand hydrolysis attack during autoclaving are found in Group 1. The composition of these glasses is selected such that diffusion effects (e.g., of alkalis) from the core glass to the cladding glass or segregation at the interface between core glass and cladding glass are avoided.

The fact that the named core glasses can be provided with cladding glasses, particularly in the rigid embodiment described later, is not self-evident and is surprising, because in the case of rigid light guides, a very much better adaptation of the cladding glass to the core glass must result, since otherwise mechanical stresses can lead to a chipping of the cladding glasses and/or to a break in the core glasses, and thus to a damaging of the light guide.

The transformation temperature $T_g$ of the named cladding glasses is approximately 70 to 100 K above that of the described core glasses, by means of which a stable manufacturing process and a symmetrical shape of the light guide can be achieved. If this is not the case, a wrinkling results, which can lead to capillaries in the later drawing process of the metered goods. The value of the coefficient of thermal expansion a of the cladding glass lies in the range of 4 to $8 \cdot 10^{-6}\ K^{-1}$, while that of the core glass is in the range of 7 to $10 \cdot 10^{-6}\ K^{-1}$, so that the cladding is subjected to a compressive stress during cooling, which particularly increases the mechanical strength.

The light guide preferably contains a fiber bundle made of a plurality of individual fibers, each of which has a core made of the above-named glass systems and preferably has a cladding made of the described cladding-glass variants. Light guides of this type that contain such a fiber bundle composed of individual fibers, with or without a cladding, are named multi-core rods if they are present as rigid light guides. Each individual fiber in such a multi-core rod is rigid in and of itself in the majority of cases. Whether an individual fiber and thus the light guide is rigid or flexible is particularly dependent on the diameter of the individual fibers.

Starting from a diameter typically of approximately 0.8 mm, individual rigid fibers are assumed.

It is likewise possible that the system composed of the plurality of individual fibers with or without their cladding glasses is in turn ensheathed by a cladding glass that can correspond in particular to the previously described cladding glasses. This outer cladding glass in this case ensheathing the plurality of individual fibers is generally named sheathing glass.

The light guide is particularly preferably a rigid light guide. This can be achieved in the simplest way if the light guide is a solid glass rod or single-core rod. It is likewise possible to construct rigid light guides from the above-named fiber bundles with or without cladding. In this case, the individual fibers with or without cladding are generally pre-shaped by pulling and sintered and/or fused together.

Particularly preferred, the rigid light guide has at least one bend. This especially means that it deviates from the straight line of its longitudinal axis at any desired site. This can be achieved by subsequent pressing and/or bending of the light guide, as needed.

The acceptance angle of the light guide for the electromagnetic radiation irradiated into it in the operating state particularly depends on the refractive index $n_d$ of the core glass and of the cladding glass of the light guide. Acceptance angles of 45° to 130° are preferred. Advantageous lower limits are also 75° and/or 85°. The acceptance angle plays a large role in the structure of the beam path from the radiation source to the light guide. In order to avoid expensive focussing optics and/or collimators, for many fields of applications, it is attempted to make the acceptance angle as large as possible.

Particularly preferred, the radiation source comprises an LED and/or a laser diode. Thus, especially compact and/or ergonomic and/or energy-efficient illumination devices can be created. The above-described large acceptance angle of the illumination device according to the invention complies with the use of these radiation sources, since, in particular, LEDs represent punctiform light sources that emit in all spatial angles without corresponding optics.

It is also preferred, if, in the operating state of an illumination device of the invention, electromagnetic radiation that is reflected and/or emitted from the illuminated object is guided to a detection device by the light guide and/or another light guide particularly integrated in the illumination device. In this embodiment, in the operating state, the light guide guides the electromagnetic radiation emitted by the radiation source to the object being illuminated. This object in turn reflects and/or emits electromagnetic radiation. In the operating state, the electromagnetic radiation is emitted from the object being illuminated usually at a longer wavelength than the irradiation; thus it can be shifted spectrally to the excitation wavelength. The emission can be induced, in particular, by a fluorescence and/or phosphorescence of components and/or markers of the object being illuminated. The electromagnetic radiation reflected and/or emitted by the object being illuminated can be guided by the above-named light guide to a detection device, which can evaluate, in particular, the properties of the reflected and/or emitted electromagnetic radiation, e.g., its intensity and/or its spectrum and/or its wavelength at maximum intensity and/or at other intentsities. It is also possible that at least one additional light guide guides the reflected and/or emitted electromagnetic radiation to a detection device. This embodiment is particularly suitable for the above-described application of determining cell types, particularly the identification of cancer cells.

In a particularly preferred embodiment, the radiation source and/or the detection device and the at least one light guide are designed separable from one another. This permits enabling the operation, in particular, of a handpiece as a radiation-source unit using different light guides as attachments. For example, the light guides can be plugged onto the device unit having the radiation source. Thus, a device unit with the radiation source can be used for different applications that require different light guides. It is also possible in this way to sterilize light guides after use and to continue operation of the illumination device with already sterilized light guides.

Preferred applications of the illumination device according to the invention are the curing of plastics and/or use in a dental curing device and/or a device for identifying cell types, especially cancer cells, and/or in a device for recognizing caries and/or in dental handpieces and/or in dental angle pieces and/or in surgical devices and/or in diagnostic devices. Additional preferred applications, for example, relate to skin-analysis devices and otoscopes, in which such light guides are used. An expanded spectral region is also advantageous here. Light guides of this type, which are rigid or semi-flexible, i.e., heat-fused or bonded on one side and flexible on the other side, can likewise be utilized in endoscopes, in particular as endoscope components. Among others, embodiment examples include so-called tapers or conical shapes, which are designed as a single-core rod, SCR, or a multi-core rod, MCR, and in which the coupling and decoupling sides have a different geometry. An expanded spectral transmission bandwidth is also of advantage here.

Illumination devices according to the invention were produced with the named methods known to the person skilled in the art. The following embodiment examples explain the invention in more detail.

In a first embodiment, an illumination device with an LED as a radiation source was produced, in which the light guide is designed as a solid, rigid glass rod as the core (single-core rod), which is surrounded on its outer peripheral surface by a sheathing glass as cladding. This embodiment can be utilized in particular as a dental curing device. With respect to the properties of the light guide, it has turned out to be particularly advantageous that when the core glass has a typical diameter in the range of 29 to 31 mm, the diameter tolerances should be adjusted by subsequent smoothing (mechanical abrasion) to a max. ±0.05 mm tolerance. The advantage of the small diameter tolerance leads to the circumstance that only air gaps that are as small as possible form between the inner diameter of the sheathing glass and the core glass; otherwise such air gaps can act negatively on the transmission of the light guide. The sheathing glass in particular can have a wall thickness of 0.8 mm to 1.8 mm in this case.

The following system has proven to be a particularly advantageous combination of glasses for the production test of the above-named embodiment: Core glass made of the system of lead-free silicate-tin glasses with a diameter of 30.5 mm, sheathing glass from Group 1 with a wall thickness of 0.8 mm, or sheathing glass from Group 1 in combination with another sheathing glass from Group 1 and wall thickness of 1.4 mm. The wall thickness should not be selected too thin, since if it were, the electromagnetic radiation cannot be guided in the light guide due to evanescent field coupling. The conditions of total reflection are then partially abolished and so-called leakage modes produce scattered light, especially at bending sites or in conical shapes. The numerical aperture NA and thus the acceptance angle then also deviate from the theoretical value pre-defined via the difference in refractive index. If the wall thickness is too thick, the light is, in fact, well guided, so that the NA value corresponds to the theoretical value for the difference in refractive index; of course, a lower luminous flux is measured and the illumination intensity is smaller, since the active surface guiding the radiation is smaller with the same total diameter.

In a second embodiment, individual systems of light guide and surrounding cladding glass were drawn to approximately a diameter of 0.6 mm to 1 mm and subsequently tightly packed into a sheathing glass. Thereupon, pulling produces a rigid light guide, which is composed of individual fibers made of a core-cladding system and is surrounded on its outer peripheral surface by a sheathing glass. Details of this process can be taken from DE 10 2009 004 159 A1.

The above-named combination No. 1 has a high numerical aperture (NA), which leads to a very good light transmission of the total system. Also, a very good autoclaving stability can be achieved based on the very good chemical stability of the cladding glass and/or shielding glass of Group 1. Also, such a combination has a high stability in the case of manual and/or automated processing cycles. Therein, among other things, highly alkaline and/or acidic cleaning agents are used. Subsequently, a thermal disinfection can be produced with hot water of up to 95° C.

Individual examples of silicate-tin glasses can be taken from Table 1 of the Appendix. Examples of suitable cladding glasses, in particular for producing individual fibers of a multi-core rod, are listed in Table 2 of the Appendix. Table 3 of the Appendix lists combinations of cladding glasses and core glasses from Tables 1 and 2 as well as their physical properties. Therein, ÖW is the aperture angle, which was determined according to DIN [German Industrial Standard] 58141-3, and Δ ÖW is the difference in the aperture angles of the 1-m long and the 3.8-m long fibers measuring 50 μm in diameter.

Figure 2:
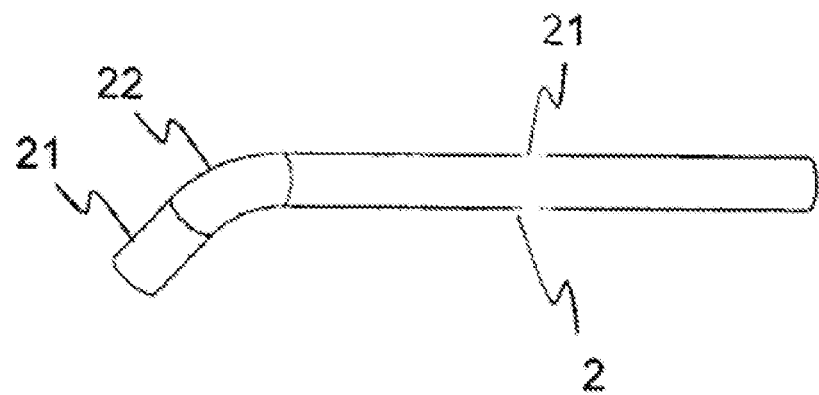
Figure 3:
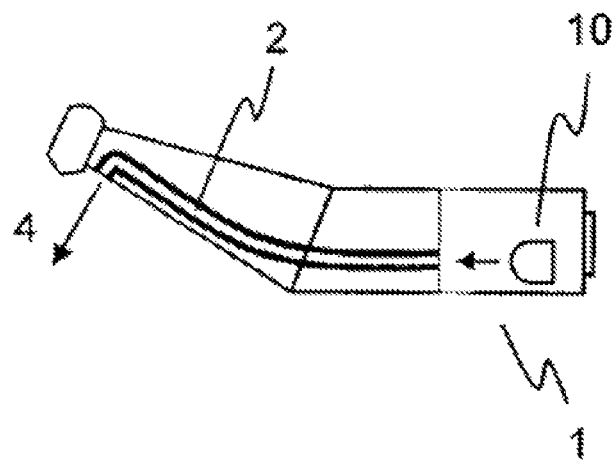
Figure 4:
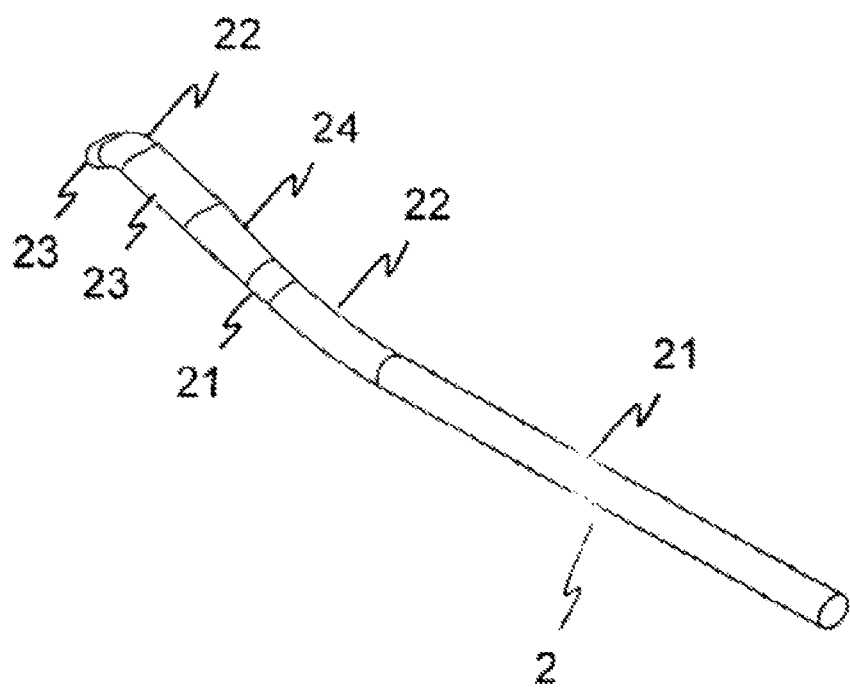
Figure 5:
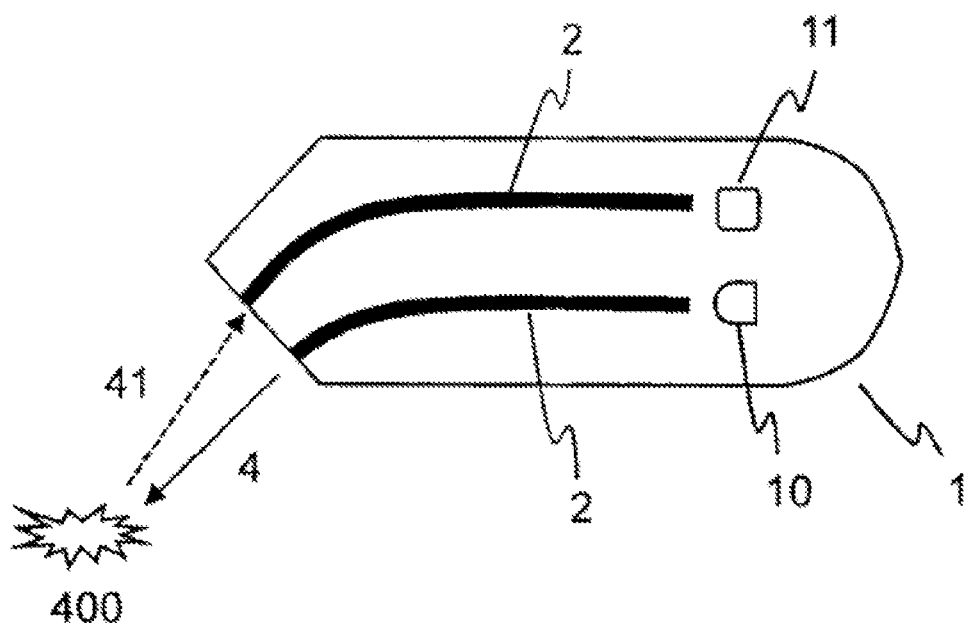
Figure 6A:
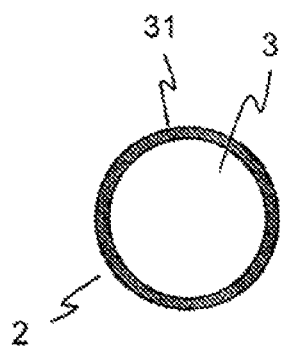
Figure 6B:
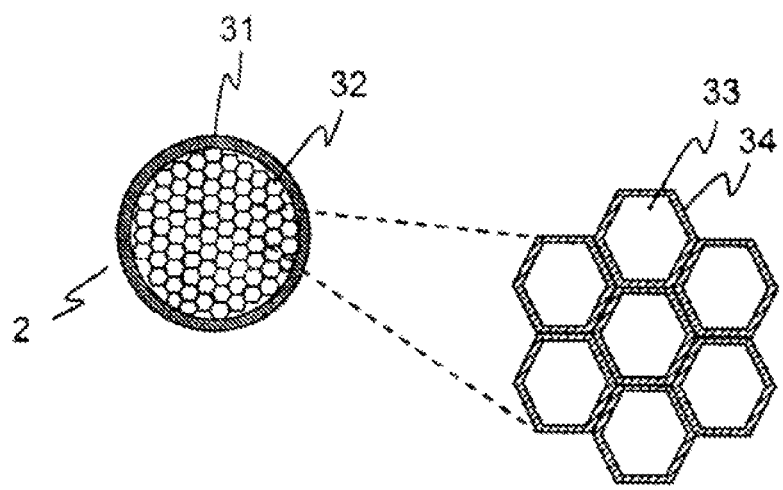
Figure 6C:
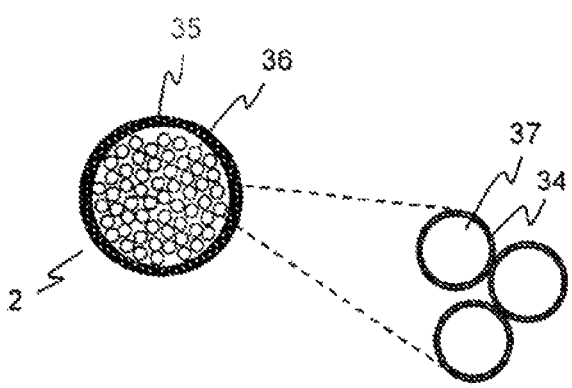
Figure 7:
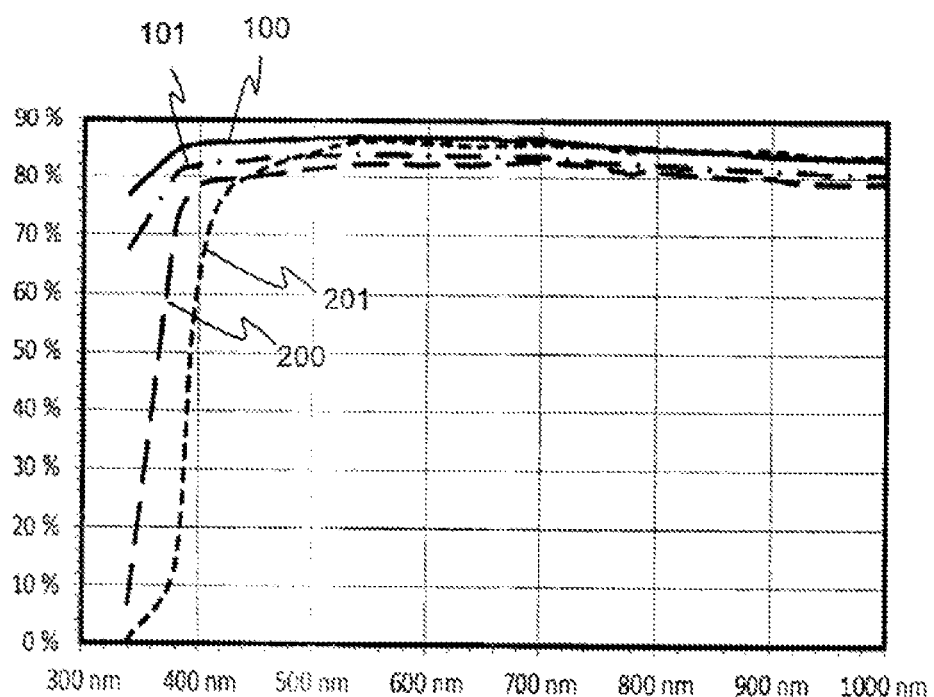
Figure 8:
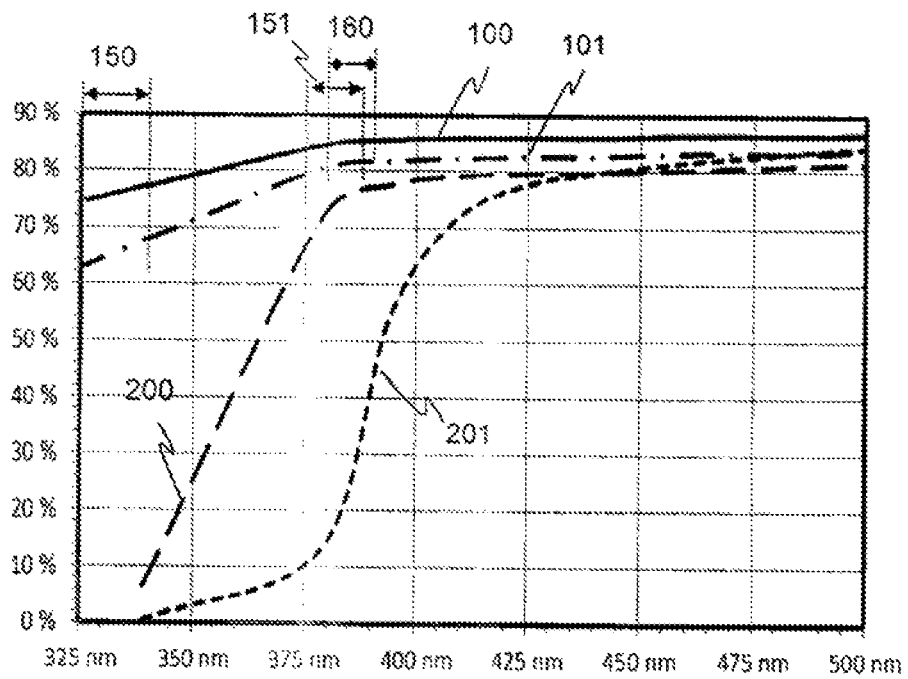

The invention is also explained in detail on the basis of the figures, which likewise represent embodiment examples. All figures are schematic; the dimensions and/or proportions of the actual objects may deviate from those in the figures. Herein is shown:

FIG. 1: a dental curing device for hardening tooth fillings;

FIG. 2: a solid glass fiber rod (single-core rod) with sheathing glass for guiding light in a dental curing device;

FIG. 3: a turbine casing for dental applications;

FIG. 4: a pressed glass fiber rod for guiding light in a turbine casing;

FIG. 5: an illumination device with detector for identifying for cell types;

FIG. 6*a*: the cross section through a solid glass rod (single-core rod) as a light guide;

FIG. 6*b*: the cross section through a light guide pulled from individual core-cladding systems (multi-core rod);

FIG. 6*c*: the cross section through another light guide pulled from individual core-cladding systems (multi-core rod);

FIG. 7: a diagram for the transmission curves;

FIG. 8: a diagram for the transmission curves.

FIG. 1 shows a typical illumination device 1 for the hardening of dental fillings, a so-called dental curing device. It contains the light guide 2 and a radiation source 10 generally accommodated in a casing; the source in this case particularly advantageously is an LED and/or a laser diode. The casing can be designed in particular as a handpiece and the light guide 2 can be designed particularly advantageously as separable from the casing.

In the operating state, the radiation source 10 emits electromagnetic radiation 4 into the front surface of the light guide 2, which guides the electromagnetic radiation 4 to the object being illuminated. After exiting the front surface of the light guide on the object side, a free beam zone is present in the operating state. Conducting the electromagnetic radiation through the light guide has the consequence that the glass material of the light guide 2 is irradiated by the electromagnetic radiation 4 in the operating state. In the example shown, the light guide 2 has a straight region 21, to which a bent region 22 is connected. The light guide 2 with these regions 21, 22 is particularly advantageously manufactured from one piece; in the example of FIG. 1, the bent region 22 was produced by heat forming, here bending.

The light guide 2 of FIG. 1 in the simplest case can be present as a solid glass rod, which is surrounded on its outer peripheral surface by at least one sheathing glass (a so-called single-core rod, SCR), but it may also be designed as a rod made of individual fibers (a so-called multi-core rod, MCR), which, as described, is formed from a plurality of individual fibers, each of which may have a cladding. The multi-core rod may also be surrounded on its outer peripheral surface by at least one sheathing glass.

The diameter of advantageous light guides 2 for application as a dental curing device generally lies in the range of 5 to 11 mm and, in addition to the cylindrical embodiment shown in FIG. 1, can also be designed in conical shape, i.e., with tapered cross section in the region of the front surface on the object side. Two variants are utilized particularly advantageously: one with clear sheathing glass from Group 1 or one with black-colored sheathing glass from Group 1.

FIG. 2 shows a light guide 2 that can be used particularly in an application according to FIG. 1. The guide is shown in a cylindrical embodiment, i.e., it has an essentially circular cross section, whose diameter is essentially the same at any place. As described above, the light guide 2 has a straight region 21, which connects to a bent region 22. A straight region 21 can then again follow this. As already described, this light guide is particularly advantageously manufactured from one piece; the shaping, here the bent region 22, can be produced by hot shaping. What has been described relative to FIG. 1 with respect to the structure of the light guide 2 as a solid single-core rod (SCR) or as a multi-core rod (MCR) applies here also. A combination of MCR and SCR is also conceivable, wherein an SCR disposed in front of the MCR in the direction of light expansion possesses a light mixing function, in order to mix, e.g., the light of a plurality of LEDs inside the radiation source 10 with respect to the components, or to homogenize the light.

FIG. 3 shows an illumination device 1 according to the invention in application as a turbine casing, in particular for dental applications. Such turbine casings are known as dental drills, among other things. The light guide 2 in this case is generally integrated in the casing. The radiation source 10 in particular can be an LED and/or laser diode, which can illuminate the treatment site via the light guide 2 in the operating state.

FIG. 4 shows a typical multi-core rod as a light guide 2 in a turbine casing, in particular according to FIG. 3. Such a multi-core rod 2 has several segments that can comprise changes in the diameter geometry, such as bends. A usually rounded cylindrical multi-core rod is used as the initial material, wherein the typical diameter of the multi-core rod is 2 to 3 mm. Subsequently, the rod is pressed into the desired geometry in a hot-forming process, wherein the rod is flattened and/or bent, at least in segments. In the figure, the cylindrical shape is maintained in the segment 21, which connects to a bent segment 22 with a circular diameter. Following this in the figure is a straight segment 21 again with identical diameter geometry. Following this, however, is the segment 24, in which a transition is produced from the circular to a flattened diameter geometry. The straight segment 23 can connect to this segment 24, whereby the diameter geometry of the previous section is maintained. Following this, according to FIG. 4, is again a bent segment 22 with the diameter geometry of the segments 24 and 23. Another straight segment 23 can follow the bent segment 22.

The production process for such a light guide is described, e.g., in DE 10 2004 034 603 B4. The end surfaces of the light guide 2 shown in FIGS. 1 to 5 are usually ground and polished. In order to assure a light guidance that is the best possible with as little loss as possible, the light guide 2 is designed particularly advantageously in each embodiment in such a way that the cross-sectional surface at any random site along its axis is of equal size.

FIG. 5 represents schematically an illumination device 1 according to the invention applied to cell-type identification. Applications are also possible, e.g., to material inspection. In this example, a radiation source 10 and a detection device 11 are integrated in a casing. In the operating state, the radiation source 10 emits electromagnetic radiation into the light guide 2 associated with it. This light guide guides the light to the object 400 being investigated. This object reflects the excitation radiation 4 guided to it by the light guide 2 and/or emits electromagnetic radiation 41, which can be, e.g., spectrally shifted to the excitation radiation 4 and/or may only comprise specific wavelengths. According to the figure, this specimen radiation 41 is guided by another light guide 2 to the detection device 41. It is likewise possible that the light guide 2 guiding the excitation radiation also guides the specimen radiation 41 back to a correspondingly disposed detection device 11. Evaluation units that can analyze the specimen radiation 41 can be associated with or integrated into the detection device 11. Particularly advantageously, an illumination device following the principle of FIG. 5 can be connected to an electronic data-processing device, which collects the data of the detection device 11 and/or performs the analysis of the specimen radiation 41 based on data of the detection device 11 and/or controls and/or monitors the radiation source 10 and thus the excitation radiation 4.

FIG. 6a represents the cross section through a light guide 2, which is formed as a solid single-core rod. The latter is composed of a core glass 3, which is ensheathed by a cladding glass 31. The cladding glass 31 is also called sheathing glass. It is also possible that more than one cladding glass 31 is found on the light guide 2. For guiding the light, the total reflection is necessary at the interface of core glass 3 to cladding glass 31, which is achieved if the refraction index of the cladding glass 31 is smaller than that of the core glass 3. This is also possible if no cladding glass is disposed around the core glass 3 and the total reflection is provided opposite air. The latter light guides, of course, are generally more sensitive to mechanical damage. The cladding glass 31 can be transparent or colored. Also possible but not shown is an embodiment in which the cladding is formed by at least one plastic material instead of by means of a glass material. All of these alternatives apply also to the embodiments of FIGS. 6b and 6c.

In FIG. 6b, the cross section through a multi-core rod as light guide 2 is shown. On the right side of the figure is shown an excerpt from the core region. As already described, a multi-core rod is composed of a plurality of individual fibers 32, here individual rigid core fibers with cladding. These individual fibers are in turn surrounded by a sheathing glass 31. As can be seen in the excerpt from the core region, the individual fibers 32 have a core 33 and a cladding 34 made of glass, whereby the refractive index of the core glass 33 is greater than that of the cladding glass 34. The embodiment shown here represents the tightest packing of individual fibers 32, which, apart from the single-core rod system shown in FIG. 6a, makes possible the maximum light-guiding surface. This is achieved by the pulling of the individual fibers 32 in the sheathing glass 31, whereby the drawing process is controlled in such a way that the individual fibers 32 fuse with one another. The hexagonal cross-sectional form of the individual fibers 32 is formed in this way. In particular, a complete fusing of the cladding regions 34 of the individual fibers 32, which thus enter into a particularly form-fitting and cohesive combination, is possible in this way. The cladding regions 34 of individual fibers 32 lying next to one another can no longer be distinguished at the combining surface. A solid bonding of the individual fibers 32 is formed, in particular. Sheathing glass 31 and cladding glass 34 advantageously should be selected such that interface reactions due to diffusion (segregation, crystal formation, etc.) do not occur.

As in FIG. 6b, FIG. 6c also shows the cross section though a light guide 2 formed as a multi-core rod. The individual fibers 36 are surrounded by a sheathing glass 35. As before, the individual fibers 36 likewise involve a core-cladding system made of a core glass 37 and a cladding glass 34, as can also be seen based on the excerpt from the core region of the light guide 2, which is shown on the right side of FIG. 6c. In contrast to the light guide according to FIG. 6b, pulling was carried out in such a way, however, that the individual fibers 36 do not completely fuse with one another. Rather, only the contact surfaces of the cladding regions 34 of individual fibers 36 lying next to one another are sintered together. In this way, in fact, a solid bonding of the individual fibers 36, which change their diameter geometry only inessentially at most, also is formed.

The spectral transmittance of the light guides 2 used in an illumination device 1 according to the invention, in comparison to light guides known from the prior art, is shown in FIG. 7 in the wavelength region from 300 nm to 1000 nm. In each case, multi-core rods that were surrounded with a sheathing glass were investigated. The relevant transmittance is plotted against the specific wavelength in FIG. 7. The transmission curves 200 and 201 show the transmission profile of light guides which are known from the prior art and which use a lead-containing glass system as core materials, and the transmission curves 100 and 101 show the transmission of light guides according to the invention composed of the named lead-free silicate-tin glasses. Based on the transmission curves, it is shown that a clearly greater transmission is measured in the blue and near UV spectral region in the light guides according to the invention. In the spectral region from 400 nm to 1000 nm, the transmission curves 100, 101 of the light guides of the system according to the invention show a nearly horizontal plateau as the maximum value, in which the transmission changes very slightly, a maximum of approximately 6%.

The light guides according to the invention of lead-free silicate-tin glasses and lead-free silicate-alkali-zinc glasses in the described composition regions show very similar spectral transmission curves to the examples represented by the curves 100 and 101. Therefore, additional curves and their association with individual glass compositions within the indicated composition regions will be omitted. The lead-free silicate-tin glasses make possible light guides with an aperture angle of approximately 45° to 130°, in particular 75° to 130°.

FIG. 8 shows the spectral transmittance of light guides in the wavelength region of 325 nm to 500 nm. FIG. 8 is an enlarged excerpt, as it were, of FIG. 7. As described relative to FIG. 7, curves 100 and 101 represent the spectral transmittance of light guides according to the invention; curves 200 and 201 represent the spectral transmission of light guides known from the prior art. Very clearly to be seen is the considerably better transmission curves 100, 101 of the light guides according to the invention compared with those of the prior art at wavelengths smaller than approximately 380 nm. At 350 nm, the spectral transmittance amounts to more than 70%, while that in the light guides known from the prior art amounts to only 25%. At a wavelength of 335 nm, the curves 200, 201 of light guides known from the prior art no longer show transmission, while those curves 100, 101 of guides according to the invention still show approximately 62% transmission available.

This leads to the circumstance that in particular, blue and UV light are attenuated less with the illumination devices according to the invention than in previously known illumination devices. Because of this and due to the above-named nearly horizontal plateau of the transmission values in the region between 400 nm and 1000 nm, the quality of the color rendering index can be increased with the illumination devices according to the invention. Likewise, new fields of application that require excitation light at wavelengths of less than approximately 380 nm open up due to the expanded useful spectrum with the illumination device according to the invention.

Wavelengths of excitation radiation 4 and/or particularly also of specimen radiation 41 that are relevant for different applications are labeled in FIG. 8. For example, a first fluorescence evaluating region 150 from 325 nm to 335 nm is of interest as specimen radiation 41 for cell-type identification. A second fluorescence evaluating region 151 extends from 375 nm to 385 nm. Additional fluorescence evaluating regions can be utilized. In the named fluorescence evaluating regions 150, 151, the light guides 2 utilized in the illumination devices 1 according to the invention, however, have the advantage of significantly better transmission than those that are known from the prior art. In particular, the shorter-wave fluorescence evaluating region 150 is inaccessible for illumination devices of the prior art.

Wavelength regions that are used for the hardening of new generations of plastics, in particular by means of dental curing devices, are also labeled in FIG. 8. Such a hardening region 160 extends from 380 nm to 390 nm. Here also, the transmission of the light guides 2 utilized in the illumination devices 1 according to the invention is higher than in those known from the prior art. In this way, the amount of radiation available per unit of time for the curing process is increased and the curing process is accelerated.

With the named glass systems, light guides 2 were produced, whose spectral transmission was maintained even during a large number of autoclaving cycles at 134° C./3 bars/10 min. holding time Even with 500 autoclaving cycles, the light guides have almost no change in transmission, which reflects a particularly high resistance to hydrolysis. The light guides of lead-containing glasses of the prior art that are the basis for the curves 200 and 201 in fact also still showed a good resistance to hydrolysis; of course, a decrease in transmission could be observed with increasing frequency of autoclaving.

Likewise, the above-named embodiment examples possess a particularly high resistance to acids or acidic media, as are used, for example, for disinfection in the medical field (e.g., peracetic acid) and/or in the assembling of medical-technical products, for example in the assembling of endoscopes (e.g., metal solders and chemical polishes).

The profile of the acceptance angle, which corresponds to the numerical aperture, was also investigated as a function of the number of automatic cleaning cycles when treating the light guide. Despite the strongly alkaline cleaning agents used here, the acceptance angle remains nearly constant, which also reflects a very good chemical resistance of the system.

Likewise, the solarization resistance of the light guides was investigated. The profile of the transmission of the light guides according to the invention was measured as a function of irradiation time with an intensive irradiation at a wavelength of 365 nm. In particular, the light guides of lead-free silicate-tin glasses have been shown to be particularly resistant to solarization.

In contrast to illumination devices of the prior art, illumination devices 1 according to the invention have the advantage that, in addition to the absence of lead in the light guides, they have a clearly improved optical transmission in the blue and the near UV spectral region, which is advantageous, on one hand, with respect to a shorter treatment time for the hardening of tooth fillings, due to a higher intensity. On the other hand, new plastic materials and hardeners can be used, since wavelengths in the UV, e.g., 365 nm, can additionally be utilized. Other possible applications result with respect to photodynamic diagnosis, i.e., identification of caries with labels, as well as photodynamic therapy.

With respect to the above-named applications, the light guides 2 of the illumination devices 1 according to the invention are also characterized by a high mechanical robustness. Also, air-bubble inclusions that otherwise can act as a disadvantage with respect to chipping and poorer optical properties can be clearly reduced or avoided with the named glass systems Conventional equipment without special adaptations can be utilized for producing the light guides in illumination devices 1 according to the invention. Required geometric tolerances can also be maintained. Likewise, post-processing procedures, such as blackening of sheathing glasses, pressing, bending and tapering, the tapering for conical shapes, etc., can be used without modification.

Tables

TABLE 1

Examples of lead-free silicate-tin glasses

| Example | 1 | 2 | 3 | 4 | 5 | 6 | 7 | 8 | 9 | 10 | 11 |
|---|---|---|---|---|---|---|---|---|---|---|---|
| $SiO_2$ | 48.79 | 42.73 | 47.71 | 48.6 | 51.8 | 33 | 47.5 | 42.8 | 4373 | 33.47 | 43.31 |
| $B_2O_3$ | | | | | 8 | 8 | | | 11.88 | 11.63 | |
| $Al_2O_3$ | 9 | 2 | | | | | | | 0.22 | 0.19 | |
| $P_2O_5$ | | | | | | | | | | | |
| $Li_2O$ | | | 0.9 | | | 1.8 | 0.82 | 0.71 | 0 | | 0.7 |
| $Na_2O$ | 9 | 6 | 8.3 | 8.2 | 9 | 4 | 6.86 | 5.8 | 5.67 | 4.9 | 5.8 |
| $K_2O$ | | | 5.8 | 9.1 | 3 | 1 | 6.48 | 3.7 | 0.66 | 0.57 | 3.7 |
| CaO | | | | | | | | | | | |
| SrO | | | | | | | | | | | |
| BaO | 20 | 28 | 0.8 | 0.8 | 22 | 22 | 0.9 | 9.2 | 29.95 | 40.24 | 9 |
| ZnO | 1 | 8 | 34.4 | 33 | 6 | 30 | 27.6 | 21.2 | 7.63 | | 21.2 |
| $La_2O_3$ | 9 | 5 | | | | | 5.64 | 10.7 | | 6.32 | 10.8 |
| $ZrO_2$ | 3 | 8 | 1.8 | | | | 3.81 | 4.9 | | 2.46 | 4.9 |
| $HfO_2$ | 0.06 | 0.17 | 0.04 | | | | 0.08 | 0.6 | | 0.05 | 0.59 |
| $SnO_2$ | 0.15 | 0.10 | 0.25 | 0.3 | 0.2 | 0.2 | 0.31 | 0.39 | 0.26 | 0.17 | 0.15 |
| MnO | | | | | | | | | | | 0.00015 |
| Total | 100 | 100 | 100 | 100 | 100 | 100 | 100 | 100 | 100 | 100 | 100 |
| Properties | | | | | | | | | | | |
| $n_d$ | 1.5828 | 1.6097 | 1.58 | 1.567 | 1.556 | 1.617 | 1.58825 | 1.62361 | 1.5830 | 1.6240 | 1.6234 |
| $\alpha_{(20\text{-}300° C.)}$ $[10^{-6}/K]$ | 7.9 | 8.1 | | | | | 8.74 | 8.22 | 8.18 | 9.25 | 7.96 |
| Tg [° C.] | 529 | 617 | | | | | 534 | 563 | 573 | 584 | 568 |

| Example | 12 | 13 | 14 | 15 | 16 | 17 | 18 | 19 | 20 |
|---|---|---|---|---|---|---|---|---|---|
| $SiO_2$ | 50 | 45 | 44 | 31.07 | 30.98 | 24.26 | 25.75 | 29.6 | 27.90 |
| $B_2O_3$ | 1 | 6 | 1 | 2.37 | 2.42 | 4.52 | 3.24 | 3.50 | 3.50 |
| $Al_2O_3$ | 1 | 4 | 2 | | | | | | |
| $P_2O_5$ | 0.1 | 4 | 2 | | | | | | |

TABLE 1-continued

Examples of lead-free silicate-tin glasses

| | | | | | | | | | |
|---|---|---|---|---|---|---|---|---|---|
| Li$_2$O | 3 | 5 | | 0.86 | 1.09 | 0.45 | 0.86 | 0.86 | 1.22 |
| Na$_2$O | 2 | 2 | 3 | 1.04 | 1.04 | | | | |
| K$_2$O | 2 | 2 | 7 | 1.55 | 1.55 | 0.28 | | | |
| CaO | 1 | 6 | 5 | | | | | | |
| SrO | | | | | | | | 0.01 | 0.02 |
| BaO | 9.9 | 6 | 8 | 22.32 | 17.96 | 34.13 | 23.16 | 16.30 | 23.20 |
| ZnO | 23 | 14 | 25 | 16.84 | 19.61 | | 14.23 | 21.60 | 16.20 |
| La$_2$O$_3$ | 5 | 5 | | 15.73 | 13.89 | 13.29 | 23.24 | 18.40 | 18.50 |
| Ta$_2$O$_5$ | | | | 3.35 | 6.50 | 21.57 | 4.58 | 4.80 | 4.70 |
| ZrO$_2$ | 2 | 1 | 3 | 4.75 | 4.81 | 1.45 | 4.84 | 4.40 | 4.30 |
| SnO$_2$ | 0.10 | 0.10 | 0.12 | 0.12 | 0.15 | 0.07 | 0.10 | 0.14 | 0.21 |
| HfO$_2$ | | | | | | 0.02 | 0.09 | 0.08 | 0.07 |
| Properties | | | | | | | | | |
| n$_d$ | 1.5739 | 1.5588 | 1.5869 | 1.68826 | 1.69171 | 1.73162 | 1.73339 | 1.70863 | 1.72019 |
| α$_{(20-300°\,C.)}$ [10$^{-6}$/K] | 7.0 | 7.9 | 7.7 | n.d. | n.d. | 8.4 | 7.71 | 6.60 | 7.51 |
| Tg [° C.] | 541 | 429 | 561 | n.d. | n.d. | 665 | 631 | 611 | 597 |

| Example | 21 | 22 | 23 | 24 | 25 | 26 | 27 | 28 | 29 | 30 |
|---|---|---|---|---|---|---|---|---|---|---|
| SiO$_2$ | 28.10 | 27.80 | 27.70 | 28.10 | 28.20 | 29.80 | 28.80 | 29.10 | 29.10 | 29.30 |
| B$_2$O$_3$ | 3.00 | 3.30 | 3.40 | 3.30 | 3.40 | 3.50 | 2.40 | 1.02 | 3.30 | 3.30 |
| Al$_2$O$_3$ | | | | | | | | | 0.02 | |
| P$_2$O$_5$ | | | | | | | | | | |
| Li$_2$O | 0.80 | 1.09 | 0.96 | 0.85 | 0.89 | 0.88 | 0.88 | 0.93 | 0.92 | 0.89 |
| Na$_2$O | | | | | | | | | | |
| K$_2$O | | | | | | | | | | |
| CaO | | | | | | | | | | |
| SrO | 0.02 | 0.02 | 0.02 | 0.02 | | 0.02 | 0.03 | 0.03 | | 0.03 |
| BaO | 28.30 | 22.50 | 22.40 | 25.40 | 28.40 | 22.00 | 29.60 | 29.60 | 29.30 | 29.60 |
| ZnO | 12.50 | 17.10 | 17.60 | 14.90 | 13.70 | 17.80 | 13.10 | 13.90 | 12.40 | 13.00 |
| La$_2$O$_3$ | 18.20 | 15.30 | 17.60 | 18.20 | 16.30 | 18.40 | 18.70 | 19.00 | 18.50 | 18.60 |
| Ta$_2$O$_3$ | 4.60 | 8.30 | 5.70 | 4.70 | 4.60 | 2.90 | 1.90 | 1.80 | 1.80 | 0.67 |
| ZrO$_2$ | 4.20 | 4.20 | 4.30 | 4.20 | 4.20 | 4.30 | 4.30 | 4.40 | 4.30 | 4.30 |
| SnO$_2$ | 0.09 | 0.14 | 0.12 | 0.10 | 0.10 | 0.10 | 0.09 | 0.10 | 0.09 | 0.09 |
| HfO$_2$ | 0.07 | 0.06 | 0.07 | 0.07 | | 0.08 | 0.08 | 0.08 | 0.08 | 0.08 |
| Properties | | | | | | | | | | |
| n$_d$ | 1.7177 | 1.7240 | 1.7211 | 1.7179 | 1.7139 | 1.7159 | 1.7145 | 1.7190 | 1.7074 | 1.7043 |
| α$_{(20-300°\,C.)}$ [10$^{-6}$/K] | 7.79 | 7.23 | 7.44 | 7.49 | 7.74 | 7.12 | 7.98 | 7.99 | 7.85 | 7.9 |
| Tg [° C.] | 624 | 602 | 613 | 623 | 612 | 600 | 631 | 646 | 618 | 610 |

TABLE 2

Examples of cladding glasses

| | Example A Group 1 | Example B Group 2 |
|---|---|---|
| Type of cladding glass | | |
| SiO$_2$ | 73.9 | 69.9 |
| B$_2$O$_3$ | 9.60 | 1.0 |
| Na$_2$O | 6.60 | 12.6 |
| K$_2$O | 2.56 | 3.2 |
| MgO | 0.01 | 2.7 |
| CaO | 0.63 | 5.1 |
| BaO | 0.04 | 2.1 |
| Al$_2$O$_3$ | 6.62 | 4.0 |
| TiO$_2$ | | 0.1 |
| F | 0.08 | 0.2 |
| Cl | | 0.18 |
| Fe$_2$O$_3$ | 0.04 | |
| Sb$_2$O$_3$ | <0.005 | |
| As$_2$O$_3$ | <0.005 | 0.1 |
| Total | 100.26 | 101 |
| Properties | | |
| n$_d$ | 1.49 | 1.514 |
| α$_{(20-300°\,C.)}$ [10$^{-6}$/K] | 5.5 | 9.1 |

TABLE 3

| Examples of core glass-cladding glass combinations | | | | | | |
|---|---|---|---|---|---|---|
| Core glass examples from Table 1 | 19 | 20 | 21 | 22 | 23 | 24 |
| Cladding glass examples from Table 2 Properties, Step index fiber | A | A | A | A | A | A |
| Attenuation 550 nm, Ø 50 μm, [dB/km] | 287 | 292 | 215 | 240 | 401 | 339 |
| Attenuation 610 nm, Ø 50 μm, [dB/km] | 374 | 411 | 306 | 333 | 469 | 386 |
| ÖW 1 m, Ø 50 μm [°] | 117 | 103 | 121 | 122 | 123 | 122 |
| ÖW 3.8 m, Ø 50 μm [°] | 99 | 83 | 113 | 104 | 108 | 113 |
| Δ ÖW between 1 m and 3.8 m, Ø 50 μm [°] | 18 | 20 | 8 | 18 | 15 | 9 |
| Core glass examples from Table 1 | 25 | 26 | 27 | 28 | 29 | 30 | 26 |
| Cladding glass examples from Table 2 Properties, Step index fiber | A | A | A | A | A | A | B |
| Attenuation 550 nm, Ø 50 μm, [dB/km] | 200 | 274 | 206 | 276 | 264 | 244 | 420 |
| Attenuation 610 nm, Ø 50 μm, [dB/km] | 275 | 373 | 313 | 357 | 424 | 393 | 490 |
| ÖW 1 m, Ø 50 μm [°] | 121 | 109 | 120 | 65 | 118 | 118 | 102 |
| ÖW 3.8 m, Ø 50 μm [°] | 113 | 100 | 113 | 54 | 114 | 112 | 84 |
| Δ ÖW between 1 m and 3.8 m, Ø 50 μm [°] | 8 | 9 | 7 | 9 | 4 | 6 | 18 |

The invention claimed is:

1. An illumination device for irradiating objects with electromagnetic radiation, comprising:
   at least one light guide; and
   a radiation source, which, in an operating state, emits electromagnetic radiation comprising at least one sector of a spectral region from 320 nm to 420 nm into the at least one light guide, wherein the at least one light guide comprises at least one lead-free silicate-tin glass that is irradiated by the electromagnetic radiation in the operating state and that has a spectral transmittance of at least 70% at a wavelength of 350 nm.

2. The illumination device according to claim 1, wherein the at least one lead-free silicate-tin glass comprises in wt. % based on oxide:

| | | |
|---|---|---|
| $B_2O_3$ | 0 | 24; |
| $SiO_2$ | 23 | 62.1; |
| $Al_2O_3$ | 0 | 10; |
| $Li_2O$ | 0 | 10; |
| $Na_2O$ | 0 | 18.5; |
| $K_2O$ | 0 | 25.7; |
| BaO | 0 | 57.8; |
| ZnO | 0 | 40; |
| $La_2O_3$ | 0 | 25; |
| $ZrO_2$ | 0 | 10; |
| $HfO_2$ | 0 | 14.2; |
| $SnO_2$ | >0 | 2; |
| MgO | 0 | 8; |
| CaO | 0 | 8; |
| SrO | 0 | 24.4; |
| $Ta_2O_5$ | 0 | 22; |
| $Y_2O_3$ | 0 | 11.9; |
| $Rb_2O$ | 0 | 15; |
| $Cs_2O$ | 0 | 21; |
| $GeO_2$ | 0 | 7.5; |
| F | 0 | 2; |
| Σ $R_2O$ | 5 | 20; and |
| Σ MgO, CaO, SrO, ZnO | 20 | 42. |

3. The illumination device according to claim 2, wherein the at least one light guide is sheathed on an outer peripheral surface by at least one cladding glass, the at least one cladding glass being selected from the group consisting of Group 1, Group 2, Group 3, and Group 4, which contains components in wt. % based on oxide:

| | Group 1 | Group 2 | Group 3 | Group 4 |
|---|---|---|---|---|
| $SiO_2$ | 70-78 | 63-75 | 75-85 | 62-70 |
| $Al_2O_3$ | 5-10 | 1-7 | 1-5 | 1-10 |
| $B_2O_3$ | 5-14 | 0-3 | 10-14 | >15 |
| $Li_2O$ | 0-2 | 0-1 | 0-3 | 0-2 |
| $Na_2O$ | 0-10 | 8-20 | 2-8 | 0-10 |
| $K_2O$ | 0-10 | 0-6 | 0-1 | 0-10 |
| MgO | 0-1 | 0-5 | 0 | 0-5 |
| CaO | 0-2 | 1-9 | 0 | 0-5 |
| SrO | 0-1 | 0 | 0 | 0-5 |
| BaO | 0-4 | 0-5 | 0 | 0-5 |
| F | 0-1 | 0-1 | 0 | 0-1 |
| Cl | 0-1 | 0-1 | 0 | 0-1 |
| $Fe_2O_3$ | 0-2 | 0-2 | 0-2 | 0-2. |

4. The illumination device according to claim 2, wherein the at least one light guide comprises a fiber bundle of a plurality of individual fibers, each of which has a core of the at least one lead-free silicate-tin glass.

5. The illumination device according to claim 4, wherein each of the plurality of individual fibers further comprises a cladding of a cladding glass selected from the group consisting of Group 1, Group 2, Group 3, and Group 4, which contains components in wt. % based on oxide:

| | Group 1 | Group 2 | Group 3 | Group 4 |
|---|---|---|---|---|
| $SiO_2$ | 70-78 | 63-75 | 75-85 | 62-70 |
| $Al_2O_3$ | 5-10 | 1-7 | 1-5 | 1-10 |
| $B_2O_3$ | 5-14 | 0-3 | 10-14 | >15 |
| $Li_2O$ | 0-2 | 0-1 | 0-3 | 0-2 |
| $Na_2O$ | 0-10 | 8-20 | 2-8 | 0-10 |
| $K_2O$ | 0-10 | 0-6 | 0-1 | 0-10 |
| MgO | 0-1 | 0-5 | 0 | 0-5 |
| CaO | 0-2 | 1-9 | 0 | 0-5 |
| SrO | 0-1 | 0 | 0 | 0-5 |
| BaO | 0-4 | 0-5 | 0 | 0-5 |
| F | 0-1 | 0-1 | 0 | 0-1 |
| Cl | 0-1 | 0-1 | 0 | 0-1 |
| $Fe_2O_3$ | 0-2 | 0-2 | 0-2 | 0-2. |

6. The illumination device according to claim 1, wherein the at least one light guide is a rigid light guide.

7. The illumination device according to claim 6, wherein the rigid light guide has at least one bend.

8. The illumination device according to claim 1, wherein the at least one light guide has an acceptance angle from 45° to 130° for the light irradiated in the operating state.

9. The illumination device according to claim 1, wherein the at least one light guide has an acceptance angle from 75° to 130° for the light irradiated in the operating state.

10. The illumination device according to claim 1, wherein the radiation source comprises at least one LED and/or at least one laser diode.

11. The illumination device according to claim 1, wherein, in the operating state, the electromagnetic radiation is guided by the at least one light guide to a detection device.

12. The illumination device according to claim 11, wherein the radiation source and/or detection device and the at least one light guide are separable from one another.

13. The illumination device according to claim 1, wherein the device is configured for a use selected from the group consisting of a plastic curing device, a dental curing device, a device for identifying cell types, a device for identifying cancer cells, a device for recognizing caries, a dental handpiece, a dental angle piece, a surgical device, a diagnostic device, a skin analysis device, an otoscope, and an endoscope.

\* \* \* \* \*